(12) United States Patent
Ninomiya et al.

(10) Patent No.: US 8,741,364 B2
(45) Date of Patent: Jun. 3, 2014

(54) METHOD OF IMPROVING FAT METABOLISM

(75) Inventors: Kiyofumi Ninomiya, Osaka (JP); Norihisa Nishida, Osaka (JP); Youichi Matsuura, Osaka (JP); Masanori Asada, Osaka (JP); Yuzo Kawahara, Osaka (JP); Masayuki Yoshikawa, Osaka (JP)

(73) Assignee: Morishita Jintan Co., Ltd., Osaka (JP)

( * ) Notice: Subject to any disclaimer, the term of this patent is extended or adjusted under 35 U.S.C. 154(b) by 1417 days.

(21) Appl. No.: 11/851,759

(22) Filed: Sep. 7, 2007

(65) Prior Publication Data

US 2008/0003312 A1 Jan. 3, 2008

Related U.S. Application Data

(62) Division of application No. 11/434,739, filed on May 16, 2006, now abandoned.

(51) Int. Cl.
*A61K 36/00* (2006.01)
*A61K 36/738* (2006.01)
*A61K 36/73* (2006.01)

(52) U.S. Cl.
USPC .................. 424/765; 424/776; 424/725

(58) Field of Classification Search
None
See application file for complete search history.

(56) References Cited

U.S. PATENT DOCUMENTS

| | | | |
|---|---|---|---|
| 4,315,944 A * | 2/1982 | Ramacci | 514/561 |
| 4,737,364 A * | 4/1988 | Kalogris | 424/195.15 |
| 4,803,069 A | 2/1989 | Kekesi et al. | |
| 5,904,924 A | 5/1999 | Gaynor et al. | |
| 6,444,221 B1 | 9/2002 | Shapiro | |
| 6,576,660 B1 * | 6/2003 | Liao et al. | 514/456 |
| 6,803,069 B2 | 10/2004 | Patnaik et al. | |
| 2002/0146400 A1 * | 10/2002 | Cincotta | 424/94.1 |
| 2002/0146404 A1 | 10/2002 | Tsuji et al. | |
| 2003/0139350 A1 | 7/2003 | Larsen et al. | |

FOREIGN PATENT DOCUMENTS

| | | |
|---|---|---|
| EP | 0787489 A2 | 8/1997 |
| EP | 1175901 A1 | 1/2002 |
| EP | 1502598 | 2/2005 |
| HU | 75907 | 5/1997 |
| JP | 09-176004 | 7/1997 |
| JP | 10-084880 | 4/1998 |
| JP | 10-330264 | 12/1998 |
| JP | 10-330278 | 12/1998 |
| JP | 2000-072642 | 3/2000 |
| JP | 2000-355538 | 12/2000 |
| JP | 2001-057869 | 3/2001 |
| JP | 2001-508801 | 7/2001 |
| JP | 2005-060366 | 3/2005 |
| JP | 2006-016312 | 1/2006 |
| JP | 2006-036788 | 2/2006 |
| WO | 9837883 | 9/1998 |

OTHER PUBLICATIONS

Definition of rose hip from Wikepedia online, pp. 1-3, accessed on Oct. 22, 2009.*
Winther et al, The anti-inflammatory properties of rose-hip, Inflammopharmacology, 7 (1): 63-68, 1999.*
BoRam et al, The effect of a potential antiobesity-supplement on weight loss and visceral fat accumulation in overweight women, Korean Journal of Nutrition, (2003) vol. 36, No. 5, pp. 483-490.*
Candiloros et al, The visceral fat reduction during weight loss with diet is proportionally higher than the body fat reduction, International Journal of Obesity, S126, P343, 2001.*
Kumarasamy et al, Bioactive flavonoid glycoside from the seeds of *Rosa canina*, Pharmaceutical Biology, (2003) vol. 41, No. 4, pp. 237-242.*
Mukhamedzanova et al, Amounts of flavonoids in various *Rosa* species growing in the Western Pamir, Khimiya Prirodnykh Soedinenii (1992), (1), 41-45.*
Gonzales et al, Dietary Rose Hip and Corn Oils Effects on Biliary and Plasma Lipid Patterns, and Hepatocyte Membranes Fluidity in Rats, Nutrition Reports International, 1989, vol. 40, No. 2, pp. 271-279.
Winther et al, Inflammopharmacology, vol. 7 No. 1, pp. 63-68, 1999.
Artur Adamczak, et al. "Flavanoid and Organic Acid Content in Rose Hips", Acta Biologica Cracoviensia Series Botanica 54/1, 2012, pp. 105-112, Polish Academy of Sciences and Jagiellonian University, Cracow.

* cited by examiner

*Primary Examiner* — Qiuwen Mi
(74) *Attorney, Agent, or Firm* — Amin, Turocy & Watson, LLP

(57) ABSTRACT

The present invention provides a fat metabolism improving agent comprising rose hips or an extract therefrom as an active ingredient. This fat metabolism improving agent is very safe and has a superior body weight reducing effect.

4 Claims, 1 Drawing Sheet

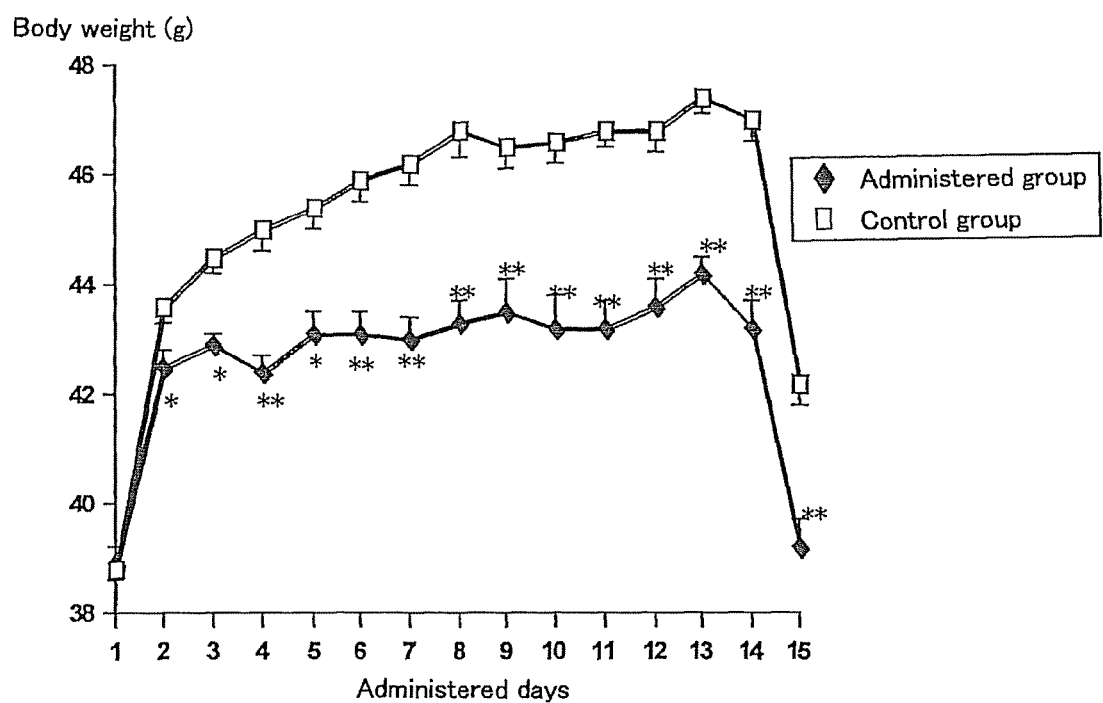

METHOD OF IMPROVING FAT METABOLISM

CROSS REFERENCE TO RELATED APPLICATIONS

This application is a divisional of U.S. application Ser. No. 11/434,739, entitled FAT METABOLISM IMPROVING AGENT and filed on May 16, 2006, which claims the benefit and priority of Japanese Patent Application No. 2004-193215 filed on Jun. 30, 2004, all of which are hereby incorporated herein by reference.

BACKGROUND OF THE INVENTION

1. Field of the Invention

The present invention relates to a fat metabolism improving agent. More specifically, the present invention relates to a fat metabolism improving agent for reducing fat in the body, in particular, fat accumulated in the viscera (visceral fat) and fat accumulated in the liver (or for improving fatty liver) by activating metabolism of lipid in the liver, which is a site for consuming fat accumulated in the body.

2. Description of the Related Art

Obesity is not only a simple cosmetic problem but also one of important risk factors in lifestyle-related diseases such as diabetes, fatty liver, hyperlipemia, and hypertension. In other words, obesity is regarded as a preliminary step leading to development of these lifestyle-related diseases. As a method for treating or preventing obesity, dietetic treatment, therapeutic exercise, pharmacotherapy, and the like have been proposed or practiced. However, all of these methods impose physical and mental pains, e.g., side effects such as disorders due to malnutrition and disturbance of motility, hunger sensation, and stress. Thus, it is difficult to preserve the effectiveness of these methods, and furthermore, these methods often are harmful to health.

For preventing obesity, numerous attempts to prevent obesity through treatments or preventive treatments in the medical field or foods consumed on a daily basis have been made heretofore. For example, as materials having an effect of promoting metabolism or consuming of fat or an effect of suppressing accumulation of body fat, extract from algae (Japanese Laid-Open Patent Publication No. 2000-72642), fruit polyphenol (Japanese Laid-Open Patent Publication No. 10-330278), conjugated polyene fatty acid (Japanese Laid-Open Patent Publication No. 2000-355538), mixture of specified amino acids and a xanthine derivative (Japanese Laid-Open Patent Publication No. 10-330264), phospholipid from soybean and egg yolk (Japanese Laid-Open Patent Publication No. 10-84880), diterpene compound (Japanese National Publication No. 2001-508801), and the like have been proposed.

However, none of these materials can provide sufficiently satisfactory obesity preventing effect or fat metabolism improving effect because, for example, the obesity preventing effect or the fat metabolism improving effect is actually small when the materials are used alone; the materials are based on the results of impractical, brief experiments; and it is necessary to ingest the materials in a large amount in regular dietary patterns.

SUMMARY OF THE INVENTION

In view of the foregoing matters, it is an object of the present invention to provide a fat metabolism improving agent that is derived from a natural product and that is capable of strongly promoting fat metabolism in biological tissues.

The present invention provides a fat metabolism improving agent comprising a polar solvent extract from the fruit of rose hips containing the seeds as an active ingredient.

In an embodiment, the fat metabolism improving agent further comprises carnitine.

The fat metabolism improving agent of the present invention is capable of strongly promoting fat metabolism in biological tissues. Therefore, it reduces body fat, in particular, fat accumulated in the viscera (especially the liver) or suppresses accumulation of fat. The fat metabolism improving agent enables a user to lose weight without the need for increasing energy consumption through exercise or decreasing energy intake through dietary restriction and without imposing mental and physical pains on the user. The fat metabolism improving agent of the present invention can provide effects for preventing development, progression, and exacerbation of various lifestyle-related diseases (diabetes, hyperlipemia, arteriosclerosis, etc.), which are triggered by obesity or fatty liver.

BRIEF DESCRIPTION OF THE DRAWINGS

FIG. 1 is a graph showing changes in the body weight when a test suspension or a comparative test suspension was administered to mice.

DESCRIPTION OF THE PREFERRED EMBODIMENTS

The fat metabolism improving agent of the present invention contains a polar solvent extract from a rose hip, which is a fruit that contains seeds (hereinafter referred to as a "seed-containing fruit of rose hip") as an active ingredient. Conventionally, it is not known that a polar solvent extract from a seed-containing fruit of rose hip has an effect of reducing body fat, in particular, visceral fat, and this is a new finding by the inventors of the present invention. When the term "visceral fat" is used, it means fat including fat in the viscera, such as the liver, the kidney, the pancreas, and the intestines, which are located in the abdominal cavity, and in the vicinity of these internal organs (e.g., around the kidney and in the vicinity of the mesentery) and epididymis fat.

The rose hip is a fruit that contains seeds and serves as a raw material of the polar solvent extract used in the present invention, and belongs to genus Rosa of plants from the family Rosaceae. Examples of the rose hip include Rosa canina (R.canina), Rosa centifolia (R. centifolia), and Rosa rugosa (R.rugosa). In the present invention, the fruit of such rose hips containing the seeds is used as a raw material of the extract. That is to say, the present invention is characterized in that the seeds of rose hips are used as a raw material of the extract, and the pseudocarp, the pericarp, or the sarcocarp of rose hips may be contained. Preferably, the seed-containing fruit of rose hip contains at least 30 wt %, more preferably at least 50 wt % of the seeds.

The polar solvent extract from a seed-containing fruit of rose hip can be obtained by extracting with a polar solvent a dried product, a broken product, a pulverized product, or a ground product of a seed-containing fruit of rose hip, a dry powder thereof, a product (e.g., granule) made by pulverizing and then shaping the dried product, or the like. The extract contains active ingredient higher than in the case where rose hips are simply used as they are, and is useful for use as foods and drinks or pharmaceutical compositions. In this specification, the term "extract" means a liquid obtained by extracting a seed-containing fruit of rose hip with a polar solvent, a diluted or a concentrated liquid therefrom, or various forms of dried products of those liquids, which will be described later.

Examples of the polar solvent used for extraction include water; alcohols such as methanol, ethanol, 1-propanol, 2-propanol, 1-butanol, and 2-butanol; ethers such as ether and tetrahydrofuran; esters such as ethyl acetate; ketones such as acetone; nitriles such as acetonitrile; hydrocarbons such as heptane; aromatic hydrocarbons such as toluene; and halogenated aliphatic hydrocarbons such as chloroform. These polar solvents can be used alone or in combination.

Among the above-mentioned polar solvents, alcohols, ethyl acetate, carbon dioxide, steam or water, and a mixed solvent of two or more of these polar solvents can be preferably used. As an alcohol, lower alcohols such as ethanol, 1-propanol, 2-propanol, 1-butanol, and 2-butanol are preferable. A mixed solvent of an alcohol and water is more preferable. For example, ethanol and water can be mixed in a volume ratio of preferably 95:5 to 5:95, more preferably 70:30 to 30:70. A higher ethanol content is preferred, and, for example, 70 v/v (volume/volume) % ethanol (ethanol:water=70:30) also can be used.

There is no particular limitation on the extraction method. It is preferable to perform extraction under conditions as mild as possible in view of safety and convenience during use. For example, a dried product of a seed-containing fruit of rose hip is pulverized, ground, or cut, and a polar solvent is added thereto in a 5- to 20-fold amount of the dried product, and then, extraction is performed for 30 minutes to 48 hours in the temperature range from 0° C. to the temperature that the polar solvent can be refluxed under conditions of shaking, stirring, refluxing, or the like. After the extraction, separating operation such as filtration, centrifugation, and the like is carried out to remove insoluble matters, and a diluting or concentrating operation is carried out, if necessary, and thus an extract can be obtained. Furthermore, optionally, it is also possible to repeat the same operations with respect to the aforementioned insoluble matters for further extraction and combine the resultant extract with the previously obtained extract to give a polar solvent extract from the seed-containing fruit of rose hip.

The obtained polar solvent extract from the seed-containing fruit of rose hip can be used as it is, or can be concentrated or dried for using. For example, the extract can be used in the forms of a liquid, a concentrate, a paste, and a dried product (e.g., a powder or a solid) thereof. Drying can be performed by a method that are commonly employed by those skilled in the art, such as spray drying, freeze drying, vacuum drying, or fluidized drying.

Optionally, the obtained extract may be shaped into the forms of a tablet, a granule, and the like using an additive agent commonly employed by those skilled in the art (e.g., excipients such as dextrin, starch, sugars, and calcium phosphate, flavors, and flavored oils), and used as foods and drinks or pharmaceutical compositions. Also, the obtained extract may be dissolved in water, a drink, or the like and used as a liquid formulation.

The daily intake of the polar solvent extract from the seed-containing fruit of rose hip for an adult person is preferably 300 to 2000 mg, more preferably 300 to 1000 mg in terms of dry weight.

The fat metabolism improving agent of the present invention contains the polar solvent extract from the seed-containing fruit of rose hip as an active ingredient. Such a fat metabolism improving agent has an effect of promoting metabolism of neutral lipid in the viscera, in particular, hepatocytes. It is well known that metabolism and burning or consuming of lipid (fat) in hepatocytes are based on beta-oxidation in mitochondria. For metabolism of fat in mitochondria to occur, it is necessary that fat is transported into the matrix of mitochondria where the reactions of beta-oxidation occur. This transportation of fat into mitochondria depends on the activity of an enzyme (carnitine palmitoyltransferase I) that works on the outer membrane of mitochondria. L-carnitine is essential for the expression of this enzyme activity, and it is known that metabolism of fat is promoted by addition of L-carnitine (Japanese Laid-Open Patent Publication No. 2001-57869). Therefore, the fat metabolism improving agent of the present invention may further contain carnitine, and as shown in Example 3 described later, metabolism of fat (neutral lipid) in hepatocytes is further promoted by combining a polar solvent extract from the seed-containing fruit of rose hip and carnitine. For example, when a fat metabolism improving agent (liquid formulation) containing a polar solvent extract from the seed-containing fruit of rose hip and carnitine is prepared, the polar solvent extract from the seed-containing fruit of rose hip can be contained in the liquid formulation in an amount of preferably at least 0.1 μg/mL, more preferably at least 1 μg/mL and carnitine can be contained in an amount of preferably at least 0.1 μg/mL, more preferably at least 1 μg/mL. Such the fat metabolism improving agent has a superior effect of promoting fat metabolism in hepatocytes.

Moreover, the fat metabolism improving agent of the present invention is used particularly as a visceral fat metabolism improving agent because it reduces visceral fat. The fat metabolism improving agent of the present invention decreases the fat content in the liver, so that it is preferable to intake (preferably orally) the fat metabolism improving agent in combination with at least one of substances having different abilities from this ability of the fat metabolism improving agent, such as a substance suppressing neutral lipid synthesis (e.g., salacia and green tea, which have a fat-synthesizing enzyme inhibiting activity), a substance having a fat absorption inhibiting effect (e.g., rosemary, sage, ginger, and cucumber, which inhibit gastrointestinal lipase activity), a substance promoting the release of fat from fat cells into the blood (e.g., citrus, hibiscus, Momordica charantia, and conjugated linoleic acid), and a substance having an effect of inhibiting alcohol absorption (e.g., laurel, the seeds of Aesculus hippocastanum, and the buds of Aralia elata). By combining-these substances, further fat reducing effect and body weight reducing effect can be obtained. Furthermore, carnitine may be added. The fat metabolism improving agent of the present invention contains a polar solvent extract from a seed-containing fruit of rose hip as an active ingredient, and it is particularly preferable to use that extract in combination with, for example, citrus and carnitine; salacia and citrus; or citrus, salacia, and rosemary.

EXAMPLES

Hereinafter, the present invention will be described in more detail by way of examples. However, the present invention is not limited to these examples.

Example 1

Fatty Acid Composition in 70% Aqueous Ethanol Extract from a Seed-Containing Fruit of Rose Hip A ground product of the fruit of rose hips (containing the seeds) was extracted at room temperature with 70% aqueous ethanol (ethanol:water=70:30 (volume ratio)) in a 10-fold amount of the ground product under shaking for 3 hours. The extraction liquid was filtrated, and then the solvent was removed by distillation under reduced pressure at a temperature of 45° C. or less to obtain an extract (this is referred to as a "rose hip extract MJ").

The fatty acid composition of this rose hip extract MJ (Lot No. 70805001) was determined by the Japan Food Research Laboratories. Table 1 shows the results.

TABLE 1

| | | Rose hip extract MJ (Rose hip seed-containing fruit) |
|---|---|---|
| Fatty acid composition | Palmitic acid | 0.05% |
| | Oleic acid | 0.01% |
| | Linoleic acid | 0.05% |
| | Linolenic acid | 0.12% |
| | Other fatty acid | Residual quantity |

As shown in Table 1, the 70% aqueous ethanol extract from the seed-containing fruit of rose hip contained 0.05% of linoleic acid and 0.12% of linolenic acid. It can be seen that the extract has a composition totally different from that of a rose hip seed oil in which main components of fatty acid are linoleic acid (49.8%) and linolenic acid (27.8%).

Example 2

Effect of Improving Fat Metabolism in Liver

Male ddY mice (at age of 6 weeks) purchased from Kiwa Laboratory Animals Co., Ltd. (Wakayama) were acclimated for approximate one week. During the acclimation period, the mice were given an MF solid diet (Oriental Yeast Co., Ltd.) as a feed and allowed to freely drink tap water. After the acclimation period, the mice were fasted for 24 hours and used for this experiment. In the experiment, seven mice each were used for test groups and a control group. To each mouse in the test groups in the fasting state, an aqueous suspension of 5% (weight/volume: w/v) gum arabic powder (Wako Pure Chemical Industries, Ltd.) containing the above-described extract MJ was administered orally (single dose) using a stomach tube such that the rose hip extract MJ (the 70% aqueous ethanol extract from the seed-containing fruit of rose hip) obtained in Example 1 was administered at 1 g/kg/body weight or 2 g/kg/body weight, and thereafter, the mice were left for 24 hours while the fasting state was further continued. To the control group, a 5 (w/v) % gum arabic aqueous solution was administered, and as is the case with the test groups, the mice were left for 24 hours while the fasting state was further continued. Then, the mice were sacrificed by cervical dislocation, and their livers were collected. The obtained liver was homogenized in a mixture of chloroform and methanol in the ratio of 2:1 (volume ratio), and then centrifuged (3000 rpm, 10 minutes) to extract lipid from the liver. Next, 25 µL of the obtained centrifugation supernatant were collected in a test tube, and warmed in a water bath at about 60° C. to remove the organic solvent. After adding 25 µL of distilled water into the test tube, the amount of neutral lipid was quantitated by Triglyceride E-test Wako (Wako Pure Chemical Industries, Ltd.) and taken as the amount of neutral lipid in hepatocytes. The measurement value was converted into the amount of neutral lipid contained in the entire liver using the weight of the tissues used for homogenization and the weight of the liver, and the amount of neutral lipid contained in the liver in the rose hip extract MJ administered groups was calculated taking the neutral lipid content in the control group as 100%. Table 2 shows the results.

The amount of neutral lipid contained in the liver was calculated in the same manner as described above, except that a commercially available rose hip seed oil (Rosehip C02-to extract) was used at 9.12 g/kg/body weight instead of the aqueous suspension of the 70% aqueous ethanol extract MJ from the seed-containing fruit of rose hip. Table 2 shows the results. It should be noted that this rose hip seed oil (Rosehip C02-to extract) contains large amounts of linoleic acid and linolenic acid and also contains an unsaturated fatty acid as a main ingredient.

TABLE 2

| | Sample | Administration amount (g/kg body weight) | Neutral lipid content in the liver (%)[1] |
|---|---|---|---|
| Test group | Rose hip extract MJ (Seed-containing fruit of rose hip) | 1 | 61 ± 3 |
| | | 2 | 44 ± 3* |
| Comparative group | Rose hip seed oil | 9.12 | 161 ± 12* |
| Control group | — | — | 100 ± 21 |

[1]Average value ± standard error
Symbol of * represents $p < 0.05$ with regard to control.

As shown in Table 2, by ingesting the 70% aqueous ethanol extract from the seed-containing fruit of rose hip, the neutral lipid content in the liver was decreased (test groups). On the other hand, when the rose hip seed oil was ingested, the neutral lipid content in the liver was increased (comparative group).

Example 3

The influence of the content of neutral lipid in primary cultured mouse hepatocytes by a rose hip extract was examined.

First, 70% aqueous ethanol (ethanol:water=70:30 (volume ratio)) was added to a pulverized product of rose hip (the fruit containing the seeds) in a 10-fold amount of the pulverized product, and the rose hip was extracted at room temperature for 3 hours while shaking. After the resultant extraction liquid was filtrated, the solvent was removed by distillation under reduced pressure at a temperature of 45° C. or less to obtain an extract. The resultant extract was dissolved in dimethylsulfoxide (DMSO), and the solution was adjusted to various extract concentrations to give sample solutions.

According to the method of Seglen (Seglen P. O., Methods Cell Biol., 13, 29-83 (1976)), hepatocytes were isolated from primary cultured cells from the mouse liver by a collagenase perfusion method. Culturing of the hepatocytes was performed using a medium (hereinafter referred to as a "medium A") prepared by adding 10% (v/v) fetal bovine serum, 100 units/mL penicillin, and 100 µg/mL streptomycin (all of which are made by Life Technologies, Inc.) to a WILLIAM'S MEDIUM E (a liquid medium made by Sigma).

The hepatic parenchymal cells (hereinafter simply referred to as the "hepatocytes") were suspended in the medium A, and seeded into a 48-well culture plate (SUMITOMO BAKELITE Co., Ltd.) at 100,000 cells/200 µL of the medium/well. The hepatocytes were cultured at 37° C. for one hour in the presence of 5% carbon dioxide. Then, 200 µL of the medium A containing 1% (v/v) of a sample solution (DMSO solution) prepared as described above was added (total: 400 µL/well, DMSO final concentration: 0.5% (v/v)) to each of the wells, and culturing was further performed at 37° C. for 20 hours in the presence of 5% carbon dioxide. It should be noted that a control group (control) was provided, in which culturing was performed in the same manner as described above, except that the medium A containing 1% (v/v) of the sample solution was replaced by a medium containing only DMSO at the same concentration (DMSO; 0.5% (v/v)), which did not contain the sample solution.

After the culturing, the hepatocytes in the culture plate were precipitated by centrifugation (2,000 rpm, 10 minutes), and thereafter the supernatant (medium) was removed. Then, 120 µL of distilled water was added to each of the wells, and then, the hepatocytes in each well were disrupted by ultrasonication. The supernatant was obtained by the centrifugation (2,000 rpm, 10 minutes), and 80 µL of the supernatant were collected to an assay plate (ASAHI TECHNO GLASS CORPORATION). The amount of neutral lipid (triglyceride) in this supernatant was quantitated by Triglyceride E-test Wako (Wako Pure Chemical Industries, Ltd.). The obtained value was taken as the amount of neutral lipid in hepatocytes. It should be noted that the experiment was conducted with n=4. An average value of the neutral lipid amount in each of the test groups and the control group was obtained, and the intracellular neutral lipid content (the ratio of the neutral lipid concentration in the test group to the neutral lipid concentration in the control group) was calculated according to the following formula.

$$\text{Intracellular neutral lipid content (\%)} = \frac{\text{Neutral lipid concentration in the test group (mg/dL)}}{\text{Neutral lipid concentration in the control group (mg/dL)}} \times 100$$

Table 3 shows the results. In Table 3, Dunnett's multiple comparison test was used to test for significant differences between the test groups and the control group. A significant level (p) of 0.05 or less was considered to be significance, and in the case of being significant, the values were shown with symbols *: p<0.05 and **:p<0.01 at the end thereof. These symbols have the same meanings as described above also in the significance level tests in tables shown below.

Comparative Example 1

DMSO solutions of an extract from the fruit of rose hips were prepared in the same manner as in Example 3, except that a ground product of the rose hips (the peel and the flesh of fruit) was used, and then, the intracellular neutral lipid content (%) was obtained in the same manner as in Example 3. Table 3 also shows the results.

TABLE 3

| | Extract concentration (µg/mL) | Intracellular neutral lipid content (%)[a] | |
|---|---|---|---|
| | | Seed-containing fruit of Rose hip (Ex. 3) | Rose hip fruit (Peel, Flesh) (Comp. Ex. 1) |
| Central group | 0 | 100 ± 9 | 100 ± 10 |
| Test group | 1 | 80 ± 4** | 87 ± 10 |
| | 3 | 71 ± 6** | 79 ± 3* |
| | 10 | 58 ± 5** | 76 ± 5* |
| | 30 | 49 ± 6** | 63 ± 4** |
| | 100 | Not measurement | 51 ± 2** |
| | 300 | Not measurement | 51 ± 5** |

[a]Average value ± standard error

From the results in Table 3, it can be seen that the polar solvent extract from the seed-containing fruit of rose hip of Example 3 reduces more neutral lipid accumulated in hepatocytes than the polar solvent extract from the rose hip fruit (the peel and the flesh of fruit) of Comparative Example 1. This indicates that a polar solvent extract from the seed-containing fruit of rose hip, in particular, a polar solvent extract from the seeds of rose hips has a superior effect of improving fat metabolism. This effect tended to decrease depending on the decrease of the concentration of the rose hip extract.

On the other hand, separately from the test, whether or not the sample solutions (containing 0.5% (v/v) of DMSO) prepared in Example 3 and Comparative Example 1 and containing 100 µg/mL of the rose hip extracts inhibit the reaction of the measuring reagent(Triglyceride E-test Wako) that was employed to quantitate neutral lipid was examined. As a result, the sample solutions containing the extracts and DMSO did not inhibit the reaction of the measuring reagent. It is clear from this fact that the rose hip extract from seed-containing fruit contributes to reducing the neutral lipid amount in hepatocytes.

Comparative Example 2

Extracts from herbs were prepared and sample solutions were prepared in the same manner as in Example 3, except that the herbs shown in Table 4 were used instead of the rose hips. Then, the neutral lipid content in hepatocytes was measured. Table 4 shows the results. It should be noted that the concentrations of the extracts from the respective herbs used for the test were 300 µg/mL.

TABLE 4

| No. | Herb extract (300 µg/ml) | Intracellular neutral lipid content (%)[a] |
|---|---|---|
| 1 | Garlic | 119 ± 5 |
| 2 | Lemon peel | 93 ± 5 |
| 3 | Red clover | 92 ± 8 |
| 4 | Coriander | 109 ± 4 |
| 5 | Orange flavor | 108 ± 8 |

[a]Average value ± standard error

None of the extracts from the herbs No. 1 to 5 shown in Table 4 significantly reduced the neutral lipid content in hepatocytes.

Example 4

Preparation of Chewable Tablet Formulation

Among components shown in Table 5 below, materials excluding the flavor, Japanese mint, thyme, and the sucrose fatty acid ester were mixed well in a mill, and then, distilled water was added thereto, and the mixture was kneaded until an appropriate viscosity with which the mixture could be shaped was obtained. Furthermore, Japanese mint, thyme, and the sucrose fatty acid ester were added thereto, and the resultant mixture was further kneaded, and finally, the flavor was added thereto. Granules were produced by extrusion granulation and dried at 40° C., and then, chewable tablets were obtained using a tablet machine. It should be noted that the 70% aqueous ethanol extract from a seed-containing fruit of rose hip in Table 5 was prepared in the same manner as in Example 1.

TABLE 5

| Component | Content |
| --- | --- |
| 70% aqueous ethanol extract from a seed-containing fruit of rose hip | 10 |
| Maltosylcyclodextrin | 14 |
| Corn starch | 11 |
| Glucose | 38 |
| Gelatin | 5 |
| Flavor | 0.2 |
| Japanese mint | 3.8 |
| Thyme | 2 |
| Anhydrous dibasic calcium phosphate | 15 |
| Sucrose fatty acid ester | 1 |
| Total | 100 (Part by weight) |

Example 5

Preparation of Health Drink

First, ingredients shown in Table 6 below were dissolved in 800 mL of distilled water, and distilled water was further added so that the total amount of the resultant solution was 1000 mL. The solution was allowed to pass through a 0.22 μm sterilization filter, and 100 mL each of the solution were packaged aseptically in brown bottles, and thus, a health drink containing 200 mg of a rose hip extract was prepared. It should be noted that the 70% aqueous ethanol extract from a seed-containing fruit of rose hip in Table 6 was prepared in the same manner as in Example 1.

TABLE 6

| Component | Content |
| --- | --- |
| 70% aqueous ethanol extract from a seed-containing fruit of rose hip | 10.0 g |
| Calcium lactate pentahydrate | 46.1 g |
| DL-Sodium tartrate | 10.0 mg |
| Succinic acid | 1.0 mL |
| Erythritol | 5.0 g |
| Citric acid | 1.2 g |
| Vitamin C | 0.5 g |
| Flavor | 1.0 mL |
| Potassium chloride | 0.1 g |
| Magnesium chloride | 50.0 mg |

The fat metabolism improving agent of the present invention is very safe because it derives from a natural herb, and has an effect of remarkably reducing body fat and visceral fat through oral administration. Therefore, the fat metabolism improving agent of the present invention is effective in preventing and treating diseases associated with obesity or fatty liver, and has a very wide range of applications.

Example 6

Effect of Improving Fat Metabolism

Male ddY mice (at age of 10 weeks) purchased from Kiwa Laboratory Animals Co., Ltd. (Wakayama) were given an MF solid feed (Oriental Yeast Co., Ltd.) and tap water for one week for acclimation. After the acclimation period, the mice were fasted for about 20 hours. Then, the body weight of each mouse was measured, and these mice were divided into a group (administered group) of six and a group (control group) of ten so that the average body weights were almost equal between the groups.

Separately, an aqueous suspension of 5% (weight/volume: w/v) gum arabic powder (Wako Pure Chemical Industries, Ltd.) containing 40 mg/mL of the rose hip extract MJ prepared in Example 1, 20 mg/mL of a citrus extract (containing 30% of synephrine), and 20 mg/mL of L-carnitine (Avocado Research Chemicals) was prepared. This suspension was used as a test suspension.

The above-described test suspension was orally administered to the mice in the administered group using a stomach tube at a rate of 10 mL/kg body weight/day for 14 days. During the administration period, the body weight and the feed intake of each mouse immediately after the test suspension was administered were measured. Furthermore, on the final day of the administration period, the mice were fasted for 20 hours, and the body weight was measured. On the other hand, the body weight and the feed intake of the mice in the control group were measured in the same manner as described above, except that an aqueous suspension of 5% gum arabic powder (referred to as a "comparative test suspension") was administered to the mice instead of the test suspension. FIG. 1 shows changes in the body weight of the mice during the administration period.

As is clear from FIG. 1, in the group (administered group) to which the test suspension containing the rose hip extract, the citrus extract, and L-carnitine was administered, the body weight gain was suppressed from the beginning of the administration when compared to the group (control group) to which the comparative test suspension that did not contain these ingredients was administered. It should be noted that there was no significant difference in the feed intake per body weight between the administered group and the control group.

Subsequently, the mice were sacrificed by ether anesthesia, and the liver and a mesenteric fat portion, a perirenal fat portion, and an epididymis fat portion in the abdominal cavity of each mouse were excised, and then the weights thereof were measured. Furthermore, the total amount of the above-mentioned fat portions was calculated as the weight of visceral fat. Table 7 shows the results.

TABLE 7

| | Liver weight (mg) | Liver/ Body weight (wt %) | Visceral fat (mg) | | | |
| --- | --- | --- | --- | --- | --- | --- |
| | | | Epididymis fat | Mesenteric fat | Perirenal fat | Total |
| Administered group | 1380 ± 32** | 3.5 ± 0.1 | 677 ± 63** | 613 ± 37** | 260 ± 28** | 1550 ± 118** |
| Control group | 1590 ± 45 | 3.8 ± 0.1 | 1281 ± 84 | 873 ± 39 | 505 ± 36 | 2658 ± 146 |

Average value ± standard error

From the results in Table 7, it can be seen that in the group (administered group) to which the test suspension containing the rose hip extract, the citrus extract, and L-carnitine was administered, the liver weight (i.e., the amount of liver fat) and the amount of visceral fat were significantly lower than those in the group (control group) to which the comparative test suspension that did not contain those ingredients was administered. Since there was no significant difference in the liver weight per body weight between the administered group and the control group, it is found that the difference in the liver weight between the administered group and the control group was not due to atrophy of the liver.

From the foregoing, it is found that an effect of suppressing fat accumulation in the liver or the viscera, that is, an effect of improving fat metabolism in the liver or the viscera can be obtained by oral intake of a rose hip extract.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method of improving visceral fat metabolism, comprising:
ingesting a polar solvent extract of both flesh and ground seed of rose hip to a subject requiring reduction of visceral fat, wherein ingestion of the polar solvent extract of both flesh and ground seed of rose hip results in the reduction of visceral fat, and wherein the polar solvent is a mixed solvent of an alcohol and water.

2. The method of claim 1, further comprising ingesting carnitine to a subject.

3. A method of improving visceral fat metabolism and promoting weight loss, comprising:
ingesting a polar solvent extract of both flesh and ground seed of rose hip to a subject requiring reduction of visceral fat and body weight, wherein ingestion of the polar solvent extract of both flesh and ground seed of rose hip results in the reduction of visceral fat and body weight, and wherein the polar solvent is a mixed solvent of an alcohol and water.

4. The method of claim 3, further comprising ingesting carnitine to a subject.

* * * * *